United States Patent [19]

Groll et al.

[11] Patent Number: 4,806,306

[45] Date of Patent: Feb. 21, 1989

[54] ATTACHMENTS IN THE FIELD OF DENTAL TECHNOLOGY MADE OF NOBLE METAL ALLOYS WITH MELTING RANGES ABOVE 1500 DEGREE CELSIUS

[75] Inventors: Werner Groll, Alzenau-Hoerstein; Rudi Steinke, Hanau; Harry Schiwiora, Pforzheim, all of Fed. Rep. of Germany

[73] Assignee: Degussa Aktiengesellschaft, Frankfurt, Fed. Rep. of Germany

[21] Appl. No.: 168,548

[22] Filed: Mar. 9, 1988

Related U.S. Application Data

[63] Continuation of Ser. No. 933,846, Nov. 24, 1986, abandoned.

[30] Foreign Application Priority Data

Dec. 3, 1985 [DE] Fed. Rep. of Germany ....... 3542641

[51] Int. Cl.$^4$ .......................... C22C 5/04; C22C 30/00
[52] U.S. Cl. .................................... 420/467; 420/466; 420/580; 433/207
[58] Field of Search ............... 420/466, 467, 468, 580; 433/207, 220, 221

[56] References Cited

U.S. PATENT DOCUMENTS 4,155,730  5/1979  Biberbach et al. .................. 420/580

FOREIGN PATENT DOCUMENTS 1950468  4/1971  Fed. Rep. of Germany ...... 420/466
 511513  8/1939  United Kingdom ................ 420/466

*Primary Examiner*—Melvin J. Andrews
*Assistant Examiner*—Robert L. McDowell
*Attorney, Agent, or Firm*—Beveridge, DeGrandi & Weilacher

[57] ABSTRACT

Noble metal alloys are used to produce attachments that can be cast-on, particularly in dental technology, having a melting range above 1500° C. The alloys comprise about 40–70% platinum, about 10–40% palladium, about 5–20% iridium, about 0.5–10% gold, about 0–13% silver and about 0–1% each of ruthenium and rhodium.

3 Claims, No Drawings

ATTACHMENTS IN THE FIELD OF DENTAL TECHNOLOGY MADE OF NOBLE METAL ALLOYS WITH MELTING RANGES ABOVE 1500 DEGREE CELSIUS

This application is a continuation of application Ser. No. 933,846, filed Nov. 24, 1986, abandoned.

The invention relates to noble metal alloys that can be cast-on or cast-to with dental alloys and have melting ranges above 1500° C. for use as attachments, particularly in the field of dental technology.

In contemporary dental technology, a multitude of different attachments are used to solve special problems in the field of dental prosthesis. For example, attachments and anchors serve to connect a removable and a fixed denture. Root posts are used to anchor crowns and bridges in devitalized teeth or strongly reduced abutments.

The connection between the attachments and the prosthesis can be achieved by soldering or casting-on with the dental alloy. In both cases, alloy formation takes place between a solid and a liquid metallic phase. However, the extent of this alloy formation can be limited to only a few layers of atoms.

Using the cast-on technique, the cast on alloy itself performs the function of the solder. Since the attachment that can be cast-on must be embedded in an investment, no fluxing agent can be used, so that only non-oxidable alloys can be employed for these attachments. Also, the solidus temperatures of these alloys must be substantially higher than the liquidus temperature of the alloy to be cast on in order to avoid melting or deformation of the attachment during the casting-on process that would deleteriously affect its function. The alloy capable of being cast-on must also have great strength and rigidity which allows the construction of small, graceful attachments. Furthermore, the alloy must have a proper cold workability for the manufacture of semi-finished products (wire, rods, etc.).

A large number of the attachments used in dental technology are made of gold-based alloys with approximately 60–70% gold and 30–40% metals of the platinum group. These alloys have great strength in the hardened state. However, their solidus temperature of approximately 1350° C. lies only slightly above the liquidus temperature of recently introduced alloys with a higher palladium content and a reduced gold content, and it lies within the range of liquidus temperatures of base metal alloys used in the dental field. Accordingly, during casting-on, one runs the risk of damaging the attachments.

The solidus temperature of a second type of alloy used for making attachments with approximately 80% platinum and 20% iridium is, at about 1800° C., considerably higher. However, these alloys are very expensive. Moreover, bubbles frequently appear at interface of the two alloys, causing a reduction of strength.

Therefore, it is an object of the present invention to provide noble metal alloys that can be cast-on and have melting ranges above 1500° C. for use as attachments, particularly in the field of dental technology. A further object of the present invention is that the mentioned alloys inoxidable and that their mechanical strength at room temperature is not diminished after the casting-on process with commonly used dental alloys or after the firing of dental ceramics, they are inexpensive; and they are not susceptible to the formation of blowholes in the connecting zone. In addition, the tensile strength of the connecting zone corresponds to at least 0.2% yield strength of the cast on alloy.

According to the invention, this object is achieved by providing noble metal alloys, comprising the following compositions; about 40–70% platinum, about 10–40% palladium, about 5–20% iridium, 0.5–10% gold, about 0–3% silver, about 0–1% ruthenium and about 0–1% rhodium.

Preferably, the alloys of the invention comprise about 50–60% platinum, about 20–30% palladium, about 10–17.5% iridium and about 2.5–7.5% gold.

Alloys containing less than 40% platinum exhibit a clear reduction in strength of the connecting zone. Because of price considerations, contents of more than 70% platinum are not interesting. Alloys containing more than 35% palladium also show a reduction in strength of the connecting zone and of the alloy.

The production of pure platinum-palladium-iridium alloys has proven to be difficult. The casting studs required, for example, for further processing into rod material or wire exhibit large blowholes in the center of the studs. These production problems can be overcome by adding up to 10% gold to the alloy. Contents of more than 10% gold lead to a noticeable deterioration of the cold working properties. Surprisingly, it has been demonstrated that gold within the concentration range as taught by the present invention clearly improves the strength and casting-on properties. While the strength of gold free alloys containing less than 15% iridium is considerably reduced during the casting-on process or during the firing of ceramics, this is not observed, or only to a lesser degree, in gold containing alloys, even with a low iridium content. This makes further cost reduction possible by reducing the content of the expensive iridium.

Greater strength is achieved by adding silver to the alloy, but at the same time a certain embrittlement appears, as well as a deterioration of the cold working properties. Therefore, the silver content in the alloys of the present invention shall not exceed 3%. Up to 1% ruthenium or rhodium may be added to the alloy at the expense of the iridium.

The alloys embodying the invention can be cast on with all commercially available dental alloys. No bubbles can be observed in the connecting zone. The tensile strength of connection zone has always been above the 0.2% yield strength of the cast on alloy. In most cases, fractures have occurred in the cast on alloy or in the alloy capable of being cast on; only in exceptional cases have fractures occurred in the connecting zone. The high solidus temperatures of the alloys which are higher than 1500° C. ensure that no melting or deformation occurs even during the casting-on process with high melting cobalt chromium alloys.

The use of these alloys is not limited to the manufacture of attachments, but it can also be extended to other parts and to other fields of application.

The present invention is further explained in detail with reference to the examples shown in the following table (Rp0.2 is the 0.2% yield strength and Rm the ultimate tensile strength):

TABLE

| COMPOSITION % by weight | | | | | Properties of Alloy: | | Tensile strength Rm/MPa of integral castings of the alloys (after simulated ceramic firing) | |
| --- | --- | --- | --- | --- | --- | --- | --- | --- |
| | | | | | Rp0.2/MPa (after | Cold | Alloy 1 | Alloy 2 |
| Pt | Pd | Ir | Au | Ag | simulated ceramic firing) | Workability | Rp0.2 ≃ 470 MPa | Rp0.2 ≃ 575 MPa |
| 60.0 | 20.0 | 19.5 | 0.5 | — | 570 ± 25 | very good | — | — |
| 47.0 | 35.0 | 17.0 | 1.0 | — | 520 ± 30 | very good | — | — |
| 57.5 | 25.0 | 15.0 | 2.5 | — | 670 ± 40 | very good | 575 ± 55 | 693 ± 50 |
| 57.5 | 25.0 | 12.5 | 5.0 | — | 750 ± 20 | good | 580 ± 33 | 670 ± 60 |
| 52.5 | 30.0 | 10.0 | 7.5 | — | 661 ± 20 | very good | 550 ± 40 | 650 ± 30 |
| 50.0 | 35.0 | 7.5 | 7.5 | — | 550 ± 20 | very good | 555 ± 7.8 | 580 ± 30 |
| 55.0 | 30.0 | 12.0 | 0.5 | 2.5 | 580 ± 40 | satisfactory | 480 ± 20 | 590 ± 40 |

Alloy 1: Au—Pd-based ceramic alloy
Casting temperature: 1400° C.
Alloy 2: Pd-based ceramic alloy
Casting temperature: 1450° C.

Further variations and modifications of the present invention will become apparent to those skilled in the art from the foregoing description and are intended to be encompassed by the claims appended hereto.

We claim:

1. An attachment in the form of a shaped body for use in the field of dental technology and adapted to connect to a dental prosthesis comprising a noble metal alloy that can be cast-on and has a melting range above 1500° C. comprising about 40–70% platinum, about 10–40% palladium, about 5–20% iridium, about 0.5–10% gold, about 0–3% silver, about 0–1% ruthenium and about 0–1% rhodium.

2. The attachment in the form of a shaped body according to claim 1, wherein the noble metal alloy comprises about 50–60% platinum, about 20–30% palladium, about 10–17.5% iridium and about 2.5–7.5% gold.

3. The attachment according to claim 1, which is in the form of a root post used to anchor crowns and bridges in dental technology.

* * * * *